United States Patent [19]
Hiramoto

[11] Patent Number: 4,464,336
[45] Date of Patent: Aug. 7, 1984

[54] METHOD OF STERILIZATION

[75] Inventor: Tatsumi Hiramoto, Himeji, Japan

[73] Assignee: Ushio Denki Kabushikikaisha, Tokyo, Japan

[21] Appl. No.: 445,042

[22] Filed: Nov. 29, 1982

Related U.S. Application Data

[63] Continuation of Ser. No. 261,270, May 6, 1981, abandoned.

[30] Foreign Application Priority Data

May 15, 1980 [JP] Japan .................................. 55-63421

[51] Int. Cl.³ ................................................ A61L 2/10
[52] U.S. Cl. ........................................ 422/24; 422/22
[58] Field of Search ....................... 422/21, 22, 23, 24; 313/225

[56] References Cited

U.S. PATENT DOCUMENTS

| | | | |
|---|---|---|---|
| 3,955,921 | 5/1976 | Tensmeyer | 422/22 |
| 4,035,691 | 7/1977 | Altman et al. | 313/225 X |
| 4,074,166 | 2/1978 | Webb et al. | 313/225 X |
| 4,190,786 | 2/1980 | Kira | 313/225 X |
| 4,199,701 | 4/1980 | Bahattacharya | 313/225 X |
| 4,237,401 | 12/1980 | Couwenberg | 313/225 |
| 4,265,747 | 5/1981 | Copa et al. | 422/23 X |

Primary Examiner—Barry S. Richman

[57] ABSTRACT

A method of sterilization effected by using a flash discharge ultraviolet lamp which provides a very large instantaneous luminescence output, destroying at an increased sterilization rate and in a reduced irradiation time microorganisms, particularly *Aspergillus nigger* and those organisms in the lower layers which have been difficult to destroy by the lamp method of the prior art.

7 Claims, 1 Drawing Figure

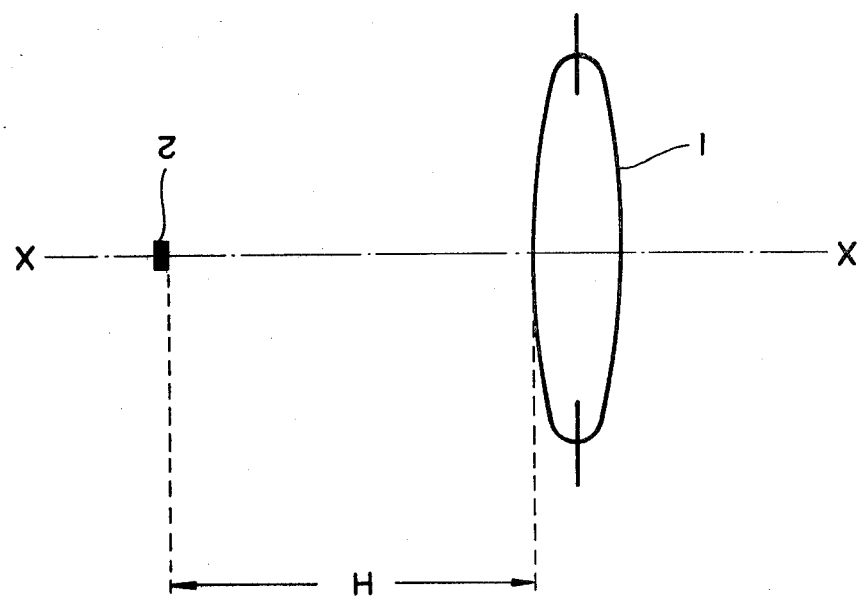

METHOD OF STERILIZATION

This is a continuation of application Ser. No. 261,270 filed May 6, 1981, now abandoned.

BACKGROUND OF THE INVENTION

1. Field of the Invention

The present invention relates to an improvement in a method of sterilization, and more particularly to an improvement in a sterilization method wherein rays emitted from a discharge lamp are applied to microorganisms to be destroyed.

2. Description of the Prior Art

One of the simple methods used heretofore for sterilization of microorganisms is irradiation by means of a sterilizer lamp.

Typical sterilizer lamps of the prior art are ones with power consumption of a few scores of watts. There are some lamps with power consumption of 200 watts or so, which, however, require a lamp length as much as 2 meters and thus do not provide a markedly increased dosage per unit arc length.

Among the large varieties of microorganisms for which the sterilizer lamp is used are those which readily absorb the rays, such as *Aspergillus nigger*. There is difficulty, however, in that when the microorganisms are present one upon another, the organisms in the lower layers are very hard to destroy in contrast to those in the upper layer. Thus, the conventional sterilizer lamp has the disadvantage that it requires a prolonged sterilization time or it attains only a limited sterilization rate for those organisms which readily absorb the rays, such as *Aspergillus nigger*.

Generally, the effectiveness of ultraviolet sterilization by means of the sterilizer lamp is given by:

$$\frac{N}{N_0} = e^{-\frac{I \cdot t}{P}}$$

$$I = I_0 \cdot e^{-\alpha x}$$

$$x = \beta \cdot N_0 \cdot l$$

where
- $N_0$ and $N$ are the number of organisms present before and after the ultraviolet irradiation, respectively,
- $e$ is the base of natural logarithm,
- $P$ is a constant specific to the organism,
- $I$ is the intensity of ultraviolet rays in the wavelength range effective for sterilizing the organisms,
- $I_0$ is the intensity of the ultraviolet rays applied to the surface layer of the organisms,
- $t$ is the irradiation time,
- $\alpha$ is the ultraviolet absorption factor of the organism,
- $\beta$ is a constant, and
- $l$ is the distance of the lamp from the surface of the upper layer of the organisms.

It is evident from these expressions that effective sterilization is attained when sufficiently large values of $I$ and $t$ are used. Since $\alpha$ and $\beta$ are constants specific to the organism to be destroyed, the effectiveness of sterilization depends upon the value of $I$ or $t$. The conventional sterilizer lamp which has a limited value of $I_0$ and hence a similarly limited value of $I$ must have recourse to an increased value of $t$, but is effective only in destroying the organisms present in the surface layer and exhibits a limited rate of sterilizing the organisms present one upon another.

SUMMARY OF THE INVENTION

An object of the present invention is to provide a novel method of sterilization which shows its effect in a short time of irradiation of destroying those microorganisms which readily absorb rays of light, such as *Aspergillus nigger*.

A feature of the present invention is to use a flash discharge lamp capable of producing a remarkable instantaneous luminescence output, instead of the conventional sterilizer lamp.

BRIEF DESCRIPTION OF THE DRAWING

A FIGURE is an illustration useful in explaining the inventive sterilization method.

DESCRIPTION OF THE PREFERRED EMBODIMENTS

Flash discharge lamps are used widely in the industry, but the one useful for executing the present invention is of the type which utilizes a rare gas as an luminous component and provides $10^4$ to $10^7$ times as much instantaneous luminescence output as that of the conventional sterilizer lamp. An experiment was conducted in which specimens containing $10^6$ cultured *Aspergillus nigger* strains per cc were placed at an irradiation distance of 10 cm from the lamp. The specimens were irradiated in the two different ways: (1) continuously for 10 seconds by a sterilizer lamp of the conventional type having an arc length of 30 cm, a bulb internal diameter of 1.2 cm, a voltage of 30 V and a current of 0.8 A, and (2) intermittently for 8 seconds at a rate of 5 emissions per second by a flash discharge lamp having an arc length of 30 cm, a bulb internal diameter of 1.2 cm, a pulse width of 1 msec. (time width of half the peak height) and a luminescence energy of 200 J/emission. The number of the organisms that survived the irradiation was $10^4$ and only 10 for methods (1) and (2) above, respectively, which correspond to the sterilization rate of 99 and 99.999%, respectively. In other words the flash discharge lamp gives a survival rate 1/1,000 that of the sterilizer lamp.

Thus, the experiment shows that the flash discharge lamp in accordance with the method of this invention attains a higher sterilization rate in a shorter irradiation time than the conventional lamp method.

The ultraviolet frequency range which is particularly effective in sterilization is 3,000 Å or less. The use of mercury, zinc, cadmium or tin sealed within the flash discharge lamp as a luminous component, together with a rare gas, will assure a higher sterilization rate in a shorter irradiation time, because these elements emit intense rays of the frequency of 3,000 Å or less.

The ultraviolet dosage from the flash discharge lamp containing a rare gas as a luminous component increases with an increase of the luminescence energy density:

$$Q = J/(D \cdot L \cdot t)$$

where
- $Q$ is the energy density,
- $J$ is the electric input for a single flash in joules,
- $D$ is the bulb internal diameter, cm
- $L$ is the arc length, cm, and
- $t$ is the pulse width at half the peak height, msec.

Thus, it is advisable to specify the value of Q. The value of Q was found to be approximately 5.6 in the mentioned experiment, but the intended sterilization at a sufficiently high rate and in a sufficiently short time is achieved if the value of Q is 0.03 or more. Even with the use of less effective 3,000 Å or greater ultraviolet rays or visible or infrared rays with actually no sterilizing efficacy, if the flash discharge lamp is allowed to instantaneously emit a large dosage, the rays absorbed into *Aspergillus nigger* are expected to heat the mold instantaneously, providing a sort of thermal sterilization. It is believed that such a thermal effect occurred without this phenomenon being evaluated in the mentioned experiment.

The FIGURE of the drawing is useful in explaining the above-noted experiment of sterilization. Reference numeral 1 is a lamp, such as a sterilizer or flash discharge lamp, X—X is a center line representing the center of the arc in the lamp 1, and numeral 2 is a specimen containing *Aspergillus nigger* which was oriented to the lamp 1 on the center line X—X.

It can be seen from the foregoing that the present invention features use of a flash discharge lamp capable of instantaneously emitting a large dosage of rays, instead of the conventional sterilizer lamp, and is advantageous in that it is substantially effective even in sterilizing microorganisms that readily absorb rays such as *Aspergillus nigger*.

What is claimed is:

1. A method of ultraviolet light sterilization comprising the steps of: (a) emitting short high intensity ultraviolet rays having a frequency of 3,000 Å or less from a flash discharge lamp containing a rare gas as a luminous component, wherein the energy density of the luminescence from the flash discharge lamp is 0.03 (J/cm$^2$ msec) or more and (b) applying the emitted short high intensity ultraviolet rays to microorganisms to be destroyed by the sterilizing effect of the ultraviolet rays.

2. The method as defined in claim 1, wherein step (a) comprises emitting rays from a flash discharge lamp containing, in addition to the rare gas, at least one metal selected from the group consisting of mercury, zinc, cadmium and tin as another luminous component.

3. The method of claim 1, wherein in step (b) the emitted light rays are applied to microorganisms which readily absorb light rays.

4. The method of claim 3, wherein the microorganisms are *Aspergillus nigger*.

5. The method of claims 1, 3 or 4, wherein the microorganisms are in layers.

6. The method of claims 3 or 4, wherein step (a) comprises emitting rays from a flash discharge lamp containing, in addition to the rare gas, at least one metal selected from the group consisting of mercury, zinc, cadmium and tin as another luminous component.

7. The method of claim 5, wherein step (a) comprises emitting rays from a flash discharge lamp containing, in addition to the rare gas, at least one metal selected from the group consisting of mercury, zinc, cadmium and tin as another luminous component.

* * * * *

UNITED STATES PATENT AND TRADEMARK OFFICE
CERTIFICATE OF CORRECTION

PATENT NO. : 4,464,336

DATED : Aug. 7, 1984

INVENTOR(S) : Hiramoto

It is certified that error appears in the above-identified patent and that said Letters Patent is hereby corrected as shown below:

Front Page, [56] References Cited, "Bahattacharya" should be --Bhattacharya--.

Column 3, line 15, "FIGURE" should be --Figure--.

Signed and Sealed this

Twenty-first Day of May 1985

[SEAL]

Attest:

DONALD J. QUIGG

Attesting Officer   Acting Commissioner of Patents and Trademarks